United States Patent [19]

Gustafson

[11] Patent Number: 4,518,714

[45] Date of Patent: May 21, 1985

[54] PROCESS FOR THE SELECTIVE PRODUCTION OF OLEFINS FROM SYNTHESIS GAS

[75] Inventor: Bruce L. Gustafson, Kingsport, Tenn.

[73] Assignee: Eastman Kodak Company, Rochester, N.Y.

[21] Appl. No.: 629,870

[22] Filed: Jul. 11, 1984

Related U.S. Application Data

[63] Continuation of Ser. No. 499,002, May 27, 1983.

[51] Int. Cl.$^3$ .............................................. C07C 1/04
[52] U.S. Cl. .................................................. 518/721
[58] Field of Search ........................................ 518/721

[56] References Cited

U.S. PATENT DOCUMENTS 4,423,156  12/1983  Büssimeier et al. .

FOREIGN PATENT DOCUMENTS 1050051  3/1979  Canada .............................. 518/721

Primary Examiner—Howard T. Mars
Attorney, Agent, or Firm—Clyde L. Tootle; David E. Cotey; D. B. Reece, III

[57] ABSTRACT

The present invention provides an improvement in processes for the selective production of α-olefins from synthesis gas. The improvement embodied in the process of the present invention comprises the use of a catalyst system which comprises palladium, iron, and zinc. The zinc component of the catalyst system is preferably provided in the form of a zinc oxide support onto which the remaining catalyst components are deposited. The reaction is conducted under conventional conditions of temperature and pressure, preferably at about 220° to 350° C. and about 50 to 500 psig.

11 Claims, No Drawings

PROCESS FOR THE SELECTIVE PRODUCTION OF OLEFINS FROM SYNTHESIS GAS

This is a continuation of application Ser. No. 499,002 filed on May 27, 1983.

BACKGROUND OF THE INVENTION

The present invention relates to an improvement in the selective production of α-olefins from synthesis gas. More particularly, the invention concerns reaction of synthesis gas in the presence of a unique catalyst system comprising palladium, iron, and zinc.

The preparation of hydrocarbons from synthesis gas (i.e., mixtures of carbon monoxide, hydrogen, and sometimes other gases, such as carbon dioxide, nitrogen oxides, etc.), has been the subject of extensive investigation. During World War II, the use of iron-based catalysts for this reaction was developed in Germany. An extensive review of this work has been provided by Storch et al. in the book entitled "The Fischer-Tropsch and Related Syntheses" (John Wiley & Sons, 1951). In general, these catalysts produced a broad range of hydrocarbons under operating conditions.

The serious disadvantage of most such processes has been the non-selective nature of the product distribution. Catalysts having acceptable activity often tend to give a wide spectrum of products. This lack of selectivity not only complicates the recovery of desired products, but results in the conversion of reactants to commercially uninteresting by-products.

More recent research has centered upon limiting the range of hydrocarbons produced. In most cases, research has centered on improving the selectivity to $C_2$ to $C_4$ range α-olefins. One approach has been to use a zeolite support to limit the hydrocarbon fraction obtained. U.S. Pat. Nos. 4,298,695 and 4,340,503 are representative of such processes. A second approach has been to employ promoters or selective poisons to limit the product distribution. See, e.g., U.S. Pat. Nos. 4,256,654, 4,242,234, and 4,172,842 wherein potassium compounds, such as potassium carbonate, are used in conjunction with an ironcontaining catalyst.

Other additives which have been used include manganese, magnesium, and alkali. Catalyst systems employing nickel, cobalt, and copper have also been reported.

The effect of zinc on iron catalysts has also been investigated, but with contradictory results. Yang and Oblad (preprints, Div. Pet. Chem., ACS meeting, Anaheim, Mar. 12–17, 1978) report that ZnO had no effect when added to an iron catalyst. Papadopoulios et al. (Bull. Soc. Chim. France, Pt. 1, 1982) report that when zinc and titanium were added to an iron catalyst, selectivity to α-olefins was improved. However, the relative contributions of zinc and titanium were not investigated.

It was further known in the art that the reaction of synthesis gas in the presence of a catalyst system comprising palladium and zinc oxide produced methanol to the virtual exclusion of hydrocarbons. Therefore, this combination of catalyst components would have been deemed to be a poor choice for the production of α-olefins.

Thus, while several varying approaches to the problem of selective production of α-olefins from synthesis gas have been reported, none has proven to be entirely satisfactory. It has now been found that α-olefins can be selectively produced from synthesis gas at advantageous rates by the use of a catalyst system which comprises palladium, iron, and zinc.

SUMMARY OF THE INVENTION

The present invention provides an improvement in a process for the selective production of α-olefins by the reaction at elevated temperature and pressure of a mixture of gases comprising carbon monoxide and hydrogen. The improvement comprises the use of a catalyst system which comprises palladium, iron, and zinc.

DETAILED DESCRIPTION OF THE INVENTION

The present invention resides in an improvement in processes for the preparation of α-olefins from hydrogen and carbon monoxide at elevated temperatures and pressures. The improvement comprises conducting the reaction in the presence of a catalyst system comprising palladium, iron, and zinc.

The improved process has been observed to provide high selectivity to $C_2$ to $C_5$ α-olefins. By employing the present process, a $C_2$ to $C_5$ α-olefin fraction typically in excess of about 50 weight percent of all products and in excess of about 70 weight percent of the $C_2$ to $C_5$ range hydrocarbons is obtained.

The zinc component of the catalyst system of the present invention may be provided in any form which gives catalytic activity under reaction conditions. Thus, the zinc component may be provided as zinc metal, zinc oxide, or other suitable zinc salts. In an especially preferred embodiment, the zinc catalyst component is provided in the form of zinc oxide which is employed as a support for the other catalyst components. It is imperative that such a zinc oxide support material be essentially free of acetate contamination. Otherwise, the activity and/or selectivity of the catalyst may suffer. Alternatively, it is contemplated that the zinc catalyst component may be deposited together with the other catalyst components onto some other known support material.

The iron and palladium catalyst components are likewise provided to the process of the present invention in a form which provides catalytic activity under reaction conditions. Preferably, the iron and palladium components are provided upon a support material which, as discussed above, most preferably comprises zinc oxide.

In the catalyst system of the present invention, the ratio of palladium:iron is about 10:1 to 1:10. Preferably, the ratio of palladium:iron is about 5:1 to 1:1 (e.g., about 2:1).

In preferred embodiments wherein iron and palladium are deposited upon a zinc oxide support, the total concentration of iron and palladium on such a support is about 0.1 to 10%. More preferably, the total concentration of palladium and iron on a zinc oxide support is about 0.5 to 5% by weight.

The individual catalyst components of the catalyst system of the present invention may be deposited onto a suitable support material (preferably, zinc oxide) by any of the techniques commonly used for catalyst preparation, such as impregnation from an organic or inorganic solution, precipitation, coprecipitation, or cation exchange. Conveniently, a solution of decomposable or reducible inorganic or organic palladium, iron, and/or zinc compounds is appropriately contacted with the support material, and the support is then dried, calcined, and heated under reducing conditions to form the catalyst system comprising zinc, iron, and palladium catalyst components. The individual catalyst components may be deposited concurrently or sequentially. Suitable metal salts include the nitrates and chlorides, among others well known in the art.

The catalyst system described above is utilized in the process of the present invention for the selective production of α-olefins by the reaction of a mixture of gases comprising carbon monoxide and hydrogen. The carbon monoxide and hydrogen reactants are preferably provided as a mixture, e.g., in the form of synthesis gas. Synthesis gas can be prepared from a wide range of hydrocarbon raw materials including natural gas, petroleum and petroleum residues, coal, etc., by well known methods such as steam reforming, partial oxidation, coal gasification, etc.

The relative amounts of hydrogen and carbon monoxide present in the reaction mixture can be varied over a wide range. However, the molar ratio of hydrogen to carbon monoxide typically is in the range of about 10:1 to 1:10. The molar ratio of hydrogen to carbon monoxide is preferably about 4:1 to 1:4, for example, about 1:2 to 2:1. Conventional synthesis gas having a molar ratio of about 1:1 is convenient and satisfactory for the process of the present invention. At higher ratios of hydrogen:carbon monoxide, selectivity to α-olefins is, to some extent, diminished; at lower ratios of hydrogen:carbon monoxide, deactivation of the catalyst has been observed to occur.

The present process can be conducted under typical conditions of temperature and pressure. For example, the reaction is preferably conducted at a temperature of about 150° to 450° C. (e.g., about 220° to 350° C.). The pressure which is employed in the process of the present invention preferably is in the range of about 10 to 10,000 psig and is most preferably about 50 to 500 psig.

It has been found that relatively low conversions favor the formation of α-olefins in the process of the present invention. Conversions less than about 50% of the carbon monoxide provided to the reaction zone are preferable, with conversions less than about 10% being especially preferred. Such conversions are conveniently achieved by employing a high space velocity correlated with other reaction variables (e.g., temperature, pressure, gas composition, catalyst, etc.). Gas hourly space velocities (volume of product gas stream, at 0° C. and 760 mm mercury pressure, per volume of catalyst per hour) greater than about $10^4$ hour$^{-1}$ are typically preferred.

While applicant does not wish to be bound by theoretical considerations, it appears that the advantageous results of the present process are due to a catalyst system which provides desirable selectivity to α-olefins at improved reaction rates. That is, it appears that the combination of zinc and iron catalyst components provide a desirable selectivity to α-olefins. The inclusion of palladium in the catalyst system is believed to give rise to an enhancement in the rate of reaction. In view of the prior art, it is surprising and unexpected that this combination of catalyst components provides an improvement in reaction rate without adversely affecting the selectivity of the reaction. There is therefore obtained a reaction process which selectively produces α-olefins at improved space-time yields.

While the present invention specifies the use of palladium, iron, and zinc catalyst components, it is contemplated that other catalyst components may be capable of being added to the claimed catalyst system without destroying the advantages of the system. The use of such augmented catalyst systems is to be considered as being within the scope of the present invention.

This invention will be further illustrated by the following Examples although it will be understood that these Examples are included merely for purposes of illustration and are not intended to limit the scope of the invention.

EXAMPLES 1-3 AND COMPARATIVE EXAMPLES 1-4

These Examples illustrate the preparation of a catalyst system comprising palladium, iron, and zinc and the advantageous results of a reaction process employing the same.

The catalysts employed in these Examples and in the Comparative Examples were prepared from Alpha ZnO by means of aqueous impregnation of the iron and/or palladium nitrates. Following impregnation, the samples were calcined in air at 200° C. The catalyst loadings were determined by atomic absorption (AA) techniques. In each Example and Comparative Example, a small portion (0.5 to 1.0 g) of catalyst was loaded into a plug flow microcatalytic reactor and was then heated in a flow of 1:1 $H_2$:CO at 100 psig to 300° C. The reaction system was held at 300° C. for one hour prior to sampling. Flow rates were adjusted to give a gas hourly space velocity of 10,000 hour$^{-1}$ or greater. The CO conversions were less than 10%.

The catalyst employed in Comparative Example 1 comprised 0.3% iron on a zinc oxide support; the catalyst employed in Example 1 comprised 0.3% iron and 1% Pd on zinc oxide. The catalyst of Comparative Example 2 comprised 1% Fe on ZnO; the catalyst of Example 2 comprised 1% Fe and 1% Pd on ZnO. The catalyst of Comparative Example 3 comprised 2.5% Fe on ZnO, while the catalyst of Example 3 comprised 2.5% Fe and 1% Pd on ZnO. Thus, Comparative Examples 1-3 utilized catalysts employing increasing amounts of iron, while the corresponding Examples utilized catalysts which additionally included 1% Pd. Comparative Example 4 employed a catalyst consisting solely of 1% Pd on ZnO. The results are given in Table I.

TABLE I

| | Catalyst | Temp. (°C.) | Pressure (psig) | $H_2$/CO | Rate of Production ($\mu$ moles g$^{-1}$ s$^{-1}$ × 10$^2$) | | | | | | | | | |
|---|---|---|---|---|---|---|---|---|---|---|---|---|---|---|
| | | | | | $CH_4$ | $C_2H_4$ | $C_2H_6$ | $C_3H_6$ | $C_3H_8$ | $C_4H_8$ | $C_4H_{10}$ | $C_5H_{10}$ | $C_5H_{12}$ | MeOH |
| Comp. Ex. 1 | 0.3% Fe/ZnO | 306 | 100 | 1 | 2.52 | 0.65 | 0.42 | 0.78 | 0.10 | 0.37 | 0.11 | 0.23 | 0.15 | 0.31 |
| Ex. 1 | 0.3% Fe, 1% Pd/ZnO | 306 | 100 | 1 | 11.00 | 2.90 | 1.50 | 3.30 | 0.43 | 1.70 | 0.48 | 0.93 | 0.45 | 0.86 |
| Comp. Ex. 2 | 1% Fe/ZnO | 300 | 100 | 1 | 12.50 | 3.34 | 1.80 | 4.77 | 0.48 | 2.54 | 0.66 | 1.68 | 0.87 | — |
| Ex. 2 | 1% Fe, 1% Pd/ZnO | 301 | 100 | 1 | 46.05 | 7.43 | 11.82 | 15.25 | 3.36 | 6.61 | 3.95 | 3.84 | 4.78 | — |
| Comp. Ex. 3 | 2.5% Fe/ZnO | 304 | 100 | 1 | 16.40 | 4.91 | 2.36 | 6.93 | 0.67 | 3.92 | 0.83 | 2.52 | 1.11 | 1.22 |
| Ex. 3 | 2.5% Fe, 1% Pd/ZnO | 300 | 100 | 1 | 47.50 | 8.99 | 11.37 | 15.99 | 2.95 | 7.12 | 3.32 | 4.29 | 4.13 | — |
| Comp. Ex. 4 | 1% Pd/ZnO | 305 | 100 | 1 | 0.31 | — | 0.01 | — | — | — | — | — | — | 7.18 |

It can be seen from a review of the data of Table I that the catalyst system of the present invention provided good selectivity to $C_2$–$C_5$ α-olefins. Moreover, the desired products were obtained at highly advantageous rates. Furthermore, methanol, an undesirable by-product, was not produced in appreciable quantities. It can further be seen by a review of the data of Table I that the catalyst systems employed in the Comparative Examples give undesirably low yields. That is, the inclusion of palladium, as exemplified by the Examples of the invention, provides a rate enhancement of the iron/zinc oxide catalyst without adversely affecting the selectivity thereof.

Comparative Example 4 additionally illustrates the undesirable results provided by a catalyst system consisting solely of palladium and zinc oxide. Such a catalyst system gives methanol, methane, and a very small amount of ethane as the sole measurable $C_1$–$C_5$ reaction products. In contrast, the process of the present invention provides advantageous selectivity to $C_2$–$C_5$ α-olefins at highly desirable rates.

The invention has been described in detail with particular reference to preferred embodiments thereof, but it will be understood that variations and modifications can be effected within the spirit and scope of the invention.

I claim:

1. In a process for the selective production of α-olefins by the reaction at elevated temperature and pressure of a mixture of gases comprising carbon monoxide and hydrogen, the improvement which comprises the use of a catalyst system comprising palladium, iron, and zinc, wherein the amount of palladium and iron present in the catalyst is about 0.1 to 10% by weight.

2. The process of claim 1 wherein the carbon monoxide conversion is less than about 10%.

3. The process of claim 1 wherein the ratio of palladium:iron is about 10:1 to 1:10.

4. The process of claim 3 wherein the ratio of palladium:iron is about 5:1 to 1:1.

5. The process of claim 4 wherein the ratio of palladium:iron is about 2:1.

6. The process of claim 1 wherein said zinc is provided as a zinc oxide support.

7. The process of claim 6 wherein said zinc oxide support is essentially free of acetate contamination.

8. The process of claim 6 wherein the total concentration of palladium and iron on the zinc oxide support is about 0.5 to 5% by weight.

9. The process of claim 1 wherein the ratio of hydrogen:carbon monoxide is about 1:1.

10. The process of claim 1 wherein the reaction is conducted at a pressure of about 10 to 10,000 psig and a temperature of about 150° to 450° C.

11. The process of claim 10 wherein the reaction is conducted at a pressure of about 50 to 500 psig and a temperature of about 220° to 350° C.

* * * * *